(12) United States Patent
Bhat et al.

(10) Patent No.: US 12,191,020 B2
(45) Date of Patent: Jan. 7, 2025

(54) PATIENT MONITORING AND TREATMENT USING ELECTRONIC TEXTILES

(71) Applicant: International Business Machines Corporation, Armonk, NY (US)

(72) Inventors: Ramprasad Bhat, Karnataka (IN); Sarbajit K. Rakshit, Kolkata (IN); Venkata Vara Prasad Karri, Andhra Pradesh (IN); Sampath Kumar Pulupula Venkata, Andhra Pradesh (IN)

(73) Assignee: International Business Machines Corporation, Armonk, NY (US)

(*) Notice: Subject to any disclaimer, the term of this patent is extended or adjusted under 35 U.S.C. 154(b) by 242 days.

(21) Appl. No.: 17/462,200

(22) Filed: Aug. 31, 2021

(65) Prior Publication Data
US 2023/0067403 A1 Mar. 2, 2023

(51) Int. Cl.
*G16H 40/67* (2018.01)
*A61B 5/00* (2006.01)
(Continued)

(52) U.S. Cl.
CPC ............ *G16H 20/30* (2018.01); *A61B 5/1114* (2013.01); *A61B 5/1124* (2013.01);
(Continued)

(58) Field of Classification Search
None
See application file for complete search history.

(56) References Cited

U.S. PATENT DOCUMENTS 10,037,672 B1 * 7/2018 Abraham ............ A61B 5/02055
2013/0085538 A1 4/2013 Volpe et al.
(Continued)

OTHER PUBLICATIONS

F. Axisa, et al. "Flexible Technologies and Smart Clothing for Citizen Medicine, Home Healthcare, and Disease Prevention", IEEE Transactions on Information Technology in Biomedicine, vol. 9, No. 3, Sep. 2005, https://www.researchgate.net/publication/7595431, 12 pages.
(Continued)

*Primary Examiner* — Gregory Lultschik
(74) *Attorney, Agent, or Firm* — Edell, Shapiro & Finnan, LLC (57) ABSTRACT

A computer system provides patient monitoring and treatment using electronic textiles. Biometric data pertaining to a user is received that is obtained over time from an electronic textile device associated with a body of the user. The biometric data is analyzed to identify positions and movements of the body. The identified positions and movements are analyzed to generate a knowledge corpus for the user that maps one or more of: positions, movements, and portions of the body to a health condition of the user. A treatment plan is generated, based on the knowledge corpus, that indicates a relatedness between the health condition of the user and the one or more positions, movements, and portions of the body. Embodiments of the present invention further include a method and program product for providing patient monitoring and treatment in substantially the same manner described above.

17 Claims, 7 Drawing Sheets

(51) Int. Cl.
A61B 5/11 (2006.01)
G16H 20/30 (2018.01)
G16H 50/20 (2018.01)
G16H 50/30 (2018.01)
G16H 50/70 (2018.01)

(52) U.S. Cl.
CPC .......... *A61B 5/4824* (2013.01); *A61B 5/6804* (2013.01); *A61B 5/746* (2013.01); *G16H 40/67* (2018.01); *G16H 50/30* (2018.01); *G16H 50/70* (2018.01); *G16H 50/20* (2018.01)

(56) References Cited

U.S. PATENT DOCUMENTS

| | | | | |
|---|---|---|---|---|
| 2014/0039351 | A1* | 2/2014 | Mix | A61G 7/057 600/587 |
| 2014/0063003 | A1* | 3/2014 | Kaula | G06T 19/00 345/419 |
| 2017/0055896 | A1* | 3/2017 | Al-Ali | A61B 5/1113 |
| 2017/0164876 | A1* | 6/2017 | Hyde | A61B 5/1118 |
| 2017/0287146 | A1* | 10/2017 | Pathak | G16H 15/00 |
| 2017/0325683 | A1* | 11/2017 | Larson | A61B 5/002 |
| 2018/0125412 | A1* | 5/2018 | Ferber | A61G 7/057 |
| 2018/0294058 | A1* | 10/2018 | Bostick | G16H 50/50 |
| 2019/0333276 | A1* | 10/2019 | Brown | A61B 90/50 |
| 2020/0335222 | A1* | 10/2020 | Winterbach | A61B 5/1124 |
| 2020/0372714 | A1* | 11/2020 | Soryal | A61B 90/36 |
| 2023/0037675 | A1* | 2/2023 | Vogtmeier | A61G 7/1065 |

OTHER PUBLICATIONS

P. Brown, "The Future of Healthcare May Reside in Your Smart Clothes", Mouser Electronics, downloaded from the Internet on Mar. 8, 2021, https://www.mouser.in/applications/healthcare-may-reside-in-smart-clothing/, 6 pages.
Disclosed Anonymously, "Photonic textile garment with biofeedback", IPCOM000166749D, Jan. 21, 2008, https://priorart.ip.com/IPCOM/000166749, 5 pages.
Disclosed Anonymously, "System to detect pain in patients who can't express themselves.", IPCOM000234008D, Jan. 7, 2014, https://priorart.ip.com/IPCOM/000234008, 5 pages.
D. Nield, "New 'Smart Threads' Can Change The Colour of Your Clothes Instantly", https://www.sciencealert.com/new-smart-threads-can-change-the-colour-of-your-clothes-instantly, May 6, 2016, 2 pages.
S. Draper, "Apple's Patent Suggests Health Tracking via Smart Clothes", Oct. 10, 2019, https://www.wearable-technologies.com/2019/10/apples-patent-suggests-health-tracking-via-smart-clothes/, 2 pages.
M. Owen, "iPhone-connected clothing that could monitor your health is being researched by Apple", Jan. 10, 2019, https://appleinsider.com/articles/19/01/10/iphone-connected-clothing-that-could-monitor-your-health-is-being-researched-by-apple, 6 pages.
S. Warwick, "Apple patent could point to "smart clothing" that measures health data", Oct. 4, 2019, https://www.imore.com/apple-patent-could-point-smart-clothing-could-measure-health-data, 6 pages.
M. Thomsen, DailyMail.com, "New patents reveals Apple may be working on 'smart clothing' that is capable of tracking blood pressure and respiration", https://www.dailymail.co.uk/sciencetech/article-7551141/New-patents-reveals-Apple-working-smart-clothing.html, Oct. 8, 2019, 6 pages.
Wikipedia, "E-textiles", https://en.wikipedia.org/wiki/E-textiles, downloaded from the internet on Mar. 8, 2021, 8 pages.
A. Kumari, "Introduction To E-clothing", https://www.technicaltextile.net/articles/introduction-to-e-clothing-8128, downloaded from the internet on Mar. 8, 2021, 5 pages.
Abu Sadat Muhammad Sayem, et al., "Review on Smart Electro-Clothing Systems (SeCSs)", https://www.mdpi.com/1424-8220/20/3/587/htm, www.mdpi.com/journal/sensors, Sensors 2020, 20, 587; doi:10.3390/s20030587, Jan. 21, 2020, 23 pages.
S. S. Verma, "Wearable Electronic Clothes", https://technicaltextile.net/articles/wearable-electronic-clothes-3420, downloaded from the internet on Mar. 9, 2021, 5 pages.
M. Baritz, et al., "Assessment of Human Bio-Behavior During Gait Process Using Lifemod Software", https://www.researchgate.net/figure/3D-coordinate-system-for-the-human-body-behavior-analysis_fig2_49612087, BRAIN. Broad Research in Artificial Intelligence and Neuroscience, ISSN 2067-3957, vol. 1, Oct. 2010, Special Issue on Advances in Applied Sciences, Eds Barna Iantovics, Marius M'aru steri, Rodica-M. Ion, Roumen Kountchev, 9 pages.
J. Geng, "Three-dimensional display technologies", Adv Opt Photonics. 2013 ; 5(4): 456-535. doi:10.1364/AOP.5.000456, NIH-PA Author Manuscript, https://www.ncbi.nlm.nih.gov/pmc/articles/PMC4269274/, 123 pages.
Microsoft Docs, "3-D Coordinate Systems", https://docs.microsoft.com/en-us/previous-versions/windows/desktop/bb324490(v%3Dvs.85), Nov. 6, 2009, 2 pages.
AZoSensors, "Using Sensors to Capture Body Movement", https://www.azosensors.com/article.aspx?ArticleID=429, Sep. 11, 2014, 4 pages.
Disabled-World.com, "Pain Scale Chart: 1 to 10 Levels", https://www.disabled-world.com/health/pain/scale.php, May 20, 2016, 7 pages.
Blog, "Hot and Cold Pain Relief", OrthoArizona, Complete Musculoskeletal Care, https://orthoarizona.org/blog/hot-and-cold-pain-relief, downloaded from the internet on Mar. 9, 2021, 4 pages.

* cited by examiner

PATIENT MONITORING AND TREATMENT USING ELECTRONIC TEXTILES

BACKGROUND

1. Technical Field

Present invention embodiments relate to electronic textiles, and more specifically, to utilizing electronic textiles to monitor patient health and to provide health care to patients.

2. Discussion of the Related Art

Electronic textiles, also referred to as e-textiles or smart textiles, refer to fabrics that enable digital components, such as sensors and other electronics, to be embedded within them. Some types of electronic textiles attach sensors to apparel, whereas other types are designed such that the woven textile themselves function as sensors. In particular, electrically-conductive fabrics can be integrated into textiles to enable a wide range of data collection, including temperature data, pressure data, stress and strain data, and the like.

SUMMARY

According to one embodiment of the present invention, a computer system provides patient monitoring and treatment using electronic textiles. Biometric data pertaining to a user is received, wherein the biometric data is obtained over time from an electronic textile device associated with a body of the user. The biometric data is analyzed to identify positions and movements of the body of the user. The identified positions and movements of the body are analyzed to generate a knowledge corpus for the user that maps one or more of: positions, movements, and portions of the body to a health condition of the user. A treatment plan is generated for the user based on the knowledge corpus, wherein the treatment plan indicates a relatedness between the health condition of the user and the one or more positions, movements, and portions of the body. Embodiments of the present invention further include a method and program product for patient monitoring and treatment using electronic textiles in substantially the same manner described above.

BRIEF DESCRIPTION OF THE DRAWINGS

Generally, like reference numerals in the various figures are utilized to designate like components.

DETAILED DESCRIPTION

Present invention embodiments relate to electronic textiles, and more specifically, to utilizing electronic textiles to monitor patient health and to provide health care to patients. Electronic textiles, also referred to as e-textiles, smart textiles, or electronic cloth, refer to woven materials that include some form of electrically-conductive material that supports sensors for data collection or even functions as a sensor itself. Thus, electronic textiles can be implemented in flexible, wearable apparel or other fabrics in order to gather data about a person of interest.

In a health care setting, it is beneficial to monitor a patient in order to determine and track the progression of any health conditions that the patient may have. While there are various options for tracking some aspects of a patient's health, such as a vital signs monitor for tracking heart rate, monitoring other health aspects like pain or mobility may require manual intervention. For example, a health care provider may request that a patient describe his or her pain with specificity to particular portions of the body and to provide an estimate of the pain level on a scale of one to ten. Moreover, if a patient is unable to communicate, it can be difficult or impossible to identify whether the patient is experiencing pain, discomfort, and/or reduced mobility with respect to any limbs, joints, or other body parts.

Present invention embodiments utilize electronic textile-based apparel for patients that enables the body positions and movements of a patient to be captured in real time to identify any pain and/or mobility issues. Biometric data can be collected from a patient using electronic textiles to observe the patient's movements and/or body positions over time and to correlate the movements and/or body positions with health conditions (e.g., pain and/or reduced or impaired mobility). Based on the correlations, a knowledge corpus can be developed, and a treatment plan can be automatically generated for the patient that describes how to provide care for the patient in a manner that does not affect or exacerbate the health conditions of the patient. Moreover, visualizations can be generated to show how to handle a patient to avoid causing the patient pain or injury, and particular portions of the patient's body can be highlighted using augmented reality or other techniques to properly inform health care providers.

Accordingly, present invention embodiments provide the practical application of improving the field of patient monitoring by automatically identifying health issues in a patient and generating a treatment plan that can minimize or eliminate further pain or injury to the patient. By detecting and visualizing portions of a patient's body that may experience pain or may have mobility issues, health care providers can provide improved care to the patient, such as better physical transport and handling of the patient during the patient's stay at a health care facility. Moreover, present invention embodiments provide health monitoring regardless of the patient's ability to communicate. Finally, patient outcomes can be used to continually improve the effectiveness of treatment plans that are generated using the knowledge corpus, thus enabling present invention embodiments to provide increasingly improved monitoring and treatment of patients over time. In particular, treatment plans can be developed using fewer computational resources (e.g., processing resources, memory resources, storage resources, etc.), as models can be updated to more accurately map body positions and movements to health conditions, thereby enabling better treatment plans to be developed more rapidly and based upon less data. Thus, present invention embodiments also provide the practical application of reducing patient stay time while promoting recuperation by minimizing or eliminating injury or pain caused to the patient during the stay.

Additionally or alternatively, present invention embodiments may track user positions and/or movements to identify positions, movements, and/or portions of a user's body that are associated with comfort or discomfort. Identification of user comfort or discomfort can be utilized to determine a user's mood or sentiment. Additionally, by identifying positions and/or movements of a user's body, user preferences for various activities can be identified, such as a user's handedness, gait or posture, and the like. Thus, present invention embodiments provide practical applications for providing feedback to a user to improve the user's performance at athletic activities, improve the user's posture, flexibility, range of motion, and the like. By identifying a user's preferred positions and/or movements of the user's body, various computer-implemented operations can be optimized for the user's preferences, such as automatically playing audio from a speaker that is situated on a particular side of a user, providing a directed flow or stream of a fluid (e.g., air or water, etc.) to a particular portion of a user, automatically adjusting a tilt setting of a motorized bed or chair of the user, automatically activating or deactivating safety devices such as airbags, approaching the user from a certain direction using a drone or other autonomous device, and the like.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
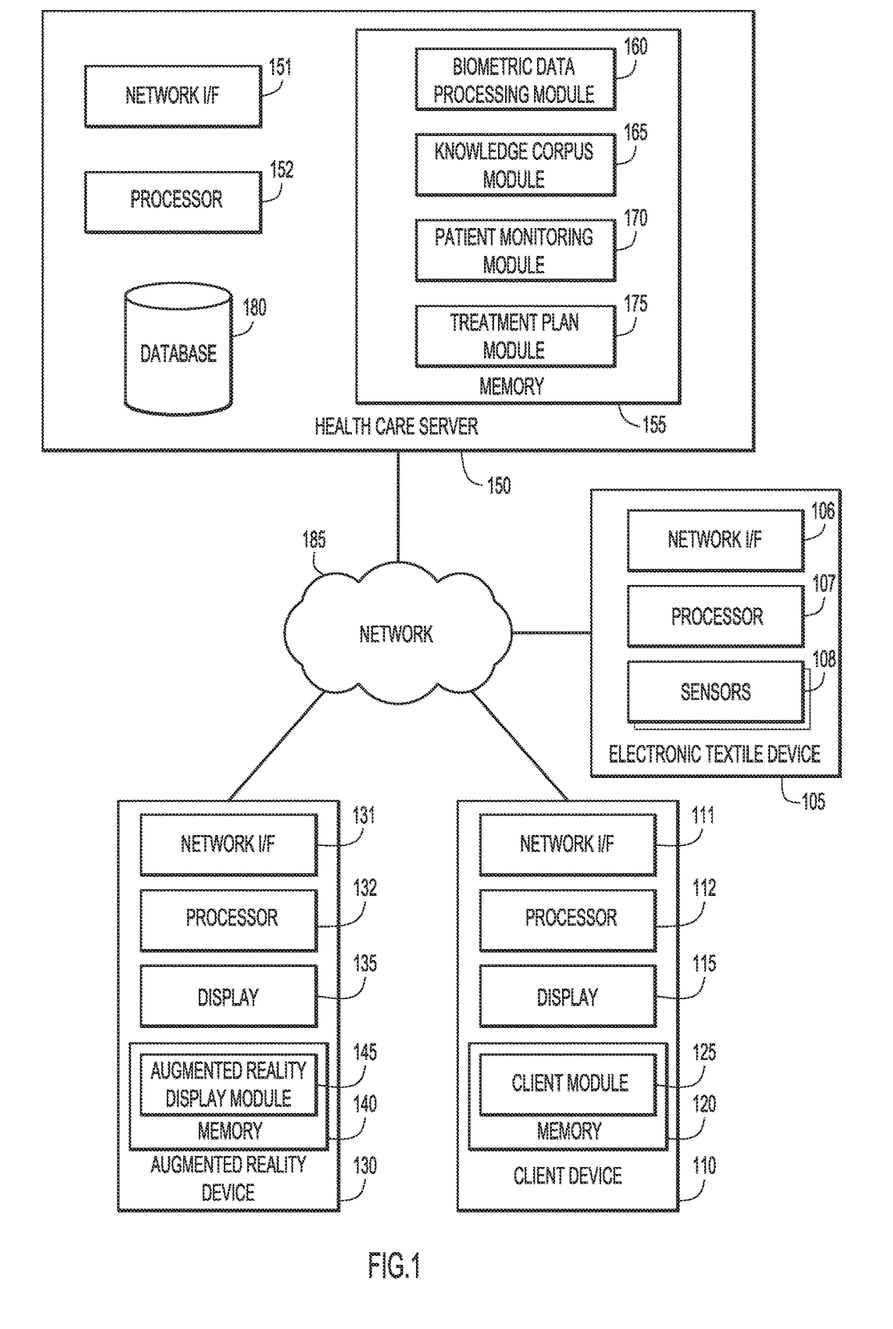
FIG. 1 is a block diagram depicting a computing environment for patient monitoring and treatment using electronic textiles in accordance with an embodiment of the present invention.

Present invention embodiments will now be described in detail with reference to the Figures. FIG. 1 is a block diagram depicting a computing environment 100 for patient monitoring and treatment using electronic textiles in accordance with an embodiment of the present invention. As depicted, computing environment 100 includes an electronic textile device 105, a client device 110, an augmented reality device 130, a user monitoring or health care server 150, and a network 185. It is to be understood that the functional division among components of computing environment 100 have been chosen for purposes of explaining present invention embodiments and is not to be construed as a limiting example.

Electronic textile device 105 includes a network interface (I/F) 106, at least one processor 107, and sensors 108. Electronic textile device 105 may include any wearable or other textile that includes sensors 108 positioned throughout the material from which data may be obtained via electrically-conductive fibers. In some embodiments, the electrically-conductive fibers may function as sensors, as certain measurable properties (e.g., conductance) may change in response to conditions such as temperature changes or application of pressure. Electronic textile device 105 may take the form of any apparel, such as a hospital gown, a shirt, pants, a jumpsuit, and the like, or other forms, such as a blanket, bedsheets, and the like. In some embodiments, electronic textile device 105 includes a long sleeved top and pants with sensors positioned throughout in order to obtain biometric data from a majority of a patient's body, including arms, legs, torso, etc. The electrically-conductive fibers of electronic textile device may include any conventional or other electronic textiles. In some embodiments, electronic textile device 105 may include organic electronics materials, including conducting and/or semiconducting materials.

Network interface 106 enables components of electronic textile device 105 to send and receive data over a network, such as network 185. Processor 107 may pre-process data obtained from sensors 108 and/or otherwise prepare data for transmission for further processing. For example, processor 107 may organize data by sensor and/or may add timestamps to data collected by sensors 108 to yield time-series data.

Sensors 108 may include any transducers for converting physical phenomena into electrical signals. In various embodiments, sensors 108 may include temperature sensors, pressure sensors, stress sensors, strain sensors, acceleration sensors, rotational sensors, and the like. Sensors 108 may be implemented by the electronic textiles of electronic textile device 105 and/or may include technologies such as microelectromechanical system (MEMS) sensors, two-dimensional nanomaterial sensors (e.g., graphene-based sensors), and the like.

Electronic textile device 105 may collect biometric data of a patient via sensors 108 when worn or otherwise associated with the patient. In particular, the biometric data can be analyzed to determine body temperatures of the patient, forces or pressure exerted on the body, a positioning or orientation of the body, including limbs, and the like. In some embodiments, the biometric data obtained from sensors 108 is analyzed in the context of a patient being in a hospital bed. For example, if sensors that are positioned on a portion of electronic textile device 105 that is in contact with a patient's left side indicate that pressure is being applied, and sensors corresponding to the patient's right side do not indicate pressure, then the biometric data may indicate that the patient is lying on his or her left side.

Client device 110 includes a network interface (I/F) 111, at least one processor 112, a display 115, and memory 120. Memory 120 includes a client module 125. Client device 110 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 111 enables components of client device 110 to send and receive data over a network, such as network 185. In general, client device 110 presents data to a user, such as a health care provider, in accordance with present invention embodiments. Client device 110 may include internal and external hardware components, as depicted and described in further detail with respect to FIG. 6.

Display 115 may include any electronic device capable of presenting information in a visual form. For example, display 115 may be a liquid crystal display (LCD), a cathode ray tube (CRT) display, a light-emitting diode (LED) display, an electronic ink display, and the like.

Client module 125 may include one or more modules or units to perform various functions of present invention embodiments described below. Client module 125 may be implemented by any combination of any quantity of software and/or hardware modules or units, and may reside within memory 120 of client device 110 for execution by a processor, such as processor 112.

Client module 125 enables treatment plan data, including visualizations, to be presented to a user (e.g., a health care provider) of client device 110. Client module 125 may receive treatment plan data from user monitoring server 150, which may be specific to one or more particular patients. The treatment plan data received and presented by client module 125 may include instructions for providing health care to a patient. In particular, the instructions may indicate the relatedness between any health condition of a patient and positions, movements, and/or portions of the body of the patient. The treatment plan may thus identify a particular portion of a patient's body, a particular position of the body, or a particular movement of the body that is either associated, or not associated, with a health condition of the patient. Thus, a health care provider will know that touching a particular portion of the patient's body (e.g., right hip), placing the patient in a particular position (e.g., right lateral recumbent), or causing the patient to perform a particular movement (e.g., bending of the right knee) may cause pain and/or injury to the patient.

The treatment plan may be presented in any format suitable for conveying the treatment plan data. In some embodiments, client module 125 may present the treatment plan in the form of text instructions. In some embodiments, the treatment plan may include one or more visualizations, including still images and/or animations, to describe the relatedness between a health condition of a patient and a position, movement, and/or portion of the body of the patient. The treatment plan may further describe the degree or magnitude of the relatedness between health conditions and positions, movements, and/or portions of the body. For example, a treatment plan may indicate that touching a patient's left shoulder is associated with a pain rating of eight out of ten, and touching the patient's left elbow is associated with a pain rating of six out of ten. Client module 125 may enable a user of client device 110 to view any other data relating to a patient in accordance with present invention embodiments, including electronic health record data, patient movement history data, and the like.

Augmented reality device 130 includes a network interface (I/F) 131, at least one processor 132, a display 135, and memory 140. Memory 140 includes an augmented reality display module 145. Augmented reality device 130 may include any programmable electronic device that is capable of executing computer readable program instructions and that includes an augmented reality display system. Network interface 131 enables components of augmented reality device 130 to send and receive data over a network, such as network 185. In general, augmented reality device 130 presents an augmented reality display to a user and enables a user to provide health care to a patient in accordance with present invention embodiments. In various embodiments, augmented reality device 130 may be a head-mounted device, a handheld device, or any other device capable of supporting augmented reality functions in accordance with present invention embodiments. Augmented reality device 130 may include internal and external hardware components, as depicted and described in further detail with respect to FIG. 6.

Display 135 may include any electronic device capable of presenting information in a visual form via an augmented reality interface. For example, display 135 may be a liquid crystal display (LCD), a cathode ray tube (CRT) display, a light-emitting diode (LED) display, an electronic ink display, and the like. In some embodiments, display 135 is a transparent or semi-transparent display, and augmented reality device 130 is mounted to a user's head such that display 135 is worn over the user's eyes and can accordingly superimpose user interface elements over the user's visual field. In some embodiments, display 135 receives real-time imagery from one or more cameras so that when a user moves the one or more cameras toward a particular view, user interface elements or other images can be superimposed over the view.

Augmented reality display module 145 presents information in a visual form to a user via display 135 to provide an augmented reality view to the user. In particular, augmented reality display module 145 may present one or more visualizations included in a treatment plan to a user (e.g., a health care provider) of augmented reality device 130. The visualizations may be presented in a manner that overlays treatment plan details for a patient over or adjacent to the patient's person. In particular, the visualizations may highlight or otherwise draw attention to the relatedness between a health condition of a patient and a position, movement, and/or portion of the body of the patient. For example, a visualization may present a highlighting or boundary around a portion of a patient's body that causes the patient pain when touched. Augmented reality display module 145 may orient the augmented reality data with respect to a patient's body by performing conventional or other object recognition techniques to identify a patient. Additionally or alternatively, augmented reality display module 145 may receive data from electronic textile device 105 that indicates anchor points that can be used to orient augmented reality visualizations with respect to a patient's body. In some embodiments, visualizations may only include movements and/or positions of the patient's body that are relevant or specific to an identified disease. Thus, visualizations may not be presented to a user that indicate potentially irrelevant movements and/or positions of the patient's body. Additionally or alternatively, by presenting visualizations that are relevant or specific to a disease, other movements and/or positions of the patient's body may not be shared to preserve patient privacy.

In some embodiments, different colors or shadings may be utilized to indicate the relatedness of portions of a patient's body to a health condition. For example, a heat map may be presented over various portions of a patient's body to indicate the relative sensitivity to pain or injury. In some embodiments, augmented reality display module 120 may display a heat map that indicates local temperatures of portions of a patient's body to other portions. For example, a color scheme may be provided that shows a user of augmented reality device 130 a blue or purple highlighting for portions of a patient's body that are cooler than average, and a red, yellow, or white highlighting for portions of a patient's body that are warmer than average.

Health care server 150 includes a network interface (I/F) 151, at least one processor 152, memory 155, and a database 180. Memory 155 may include a biometric data processing module 160, a knowledge corpus module 165, a patient monitoring module 170, and a treatment plan module 175. Health care server 150 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 151 enables components of health care server 150 to send and receive data over a network, such as network 185. In general, health care server 150 processes biometric data of patients to develop a knowledge corpus for each patient and to generate personalized treatment plans for each patient. Health care server 150 may include internal and external hardware components, as depicted and described in further detail with respect to FIG. 6.

Biometric data processing module 160, knowledge corpus module 165, user monitoring module 170, and treatment plan module 175 may include one or more modules or units to perform various functions of present invention embodiments described below. Biometric data processing module 160, knowledge corpus module 165, user monitoring module 170, and treatment plan module 175 may be implemented by any combination of any quantity of software and/or hardware modules or units, and may reside within memory 155 of health care server 150 for execution by a processor, such as processor 152.

Biometric data processing module 160 may receive biometric data collected by sensors 108 of electronic textile device 105 and process the data to identify positions and movements of the body of a patient. In some embodiments, each patient is registered with an electronic textile device that authenticates with health care sever 150 to ensure that biometric data can be securely stored on a per-patient basis. Biometric data processing module 160 may employ a rules-based approach that identifies positions and movements of individuals based on the biometric data obtained from electronic textile device 105. In some embodiments, the rules-based approach may be provided for a context in which the patient is understood to be in a bed or gurney. In particular, when the location of each sensor 108 with respect to a patient's body is known, data from the sensors can be analyzed to determine a patient's body position and identify any movements with high accuracy. A combination of higher pressure values being detected by some sensors and a lower pressure values being detected from other sensors can indicate which side of a patient's body is in contact with a bed. Biometric data processing module 160 may analyze data captured by motion sensors positioned at joints (e.g., elbow, wrist, knee, etc.) to identify movements of the patient. Pressure data may also indicate portions of a patient's body that are being touched or handled by the patient or a health care provider.

Biometric data processing module 160 may process biometric data in batches or in real-time or near real-time as the biometric data becomes available. Biometric data processing module 160 may output time-series data identifying positions and movements of a patient and associated times. For example, the time-series data may include an amount of time occupying a particular position or a time of day in which a movement is performed. The data output by biometric data processing module 160 may be provided to knowledge corpus module 165.

Knowledge corpus module 165 generates and updates a knowledge corpus for each patient in which health conditions of a patient are mapped to positions, movements, and/or portions of the patient's body. Knowledge corpus module 165 may analyze the body positions and movements of a patient over time in order to identify which positions and movements, and therefore, portions of a body, are associated with pain or injury of the patient. In particular, positions and movements can be analyzed over time to identify favored and disfavored positions and movements, and disfavored positions and movements can be associated with a health condition (e.g., pain or injury). In some embodiments, knowledge corpus module 165 may process the positions and movements of a patient in combination with other data, such as electronic health record data, to further refine or verify relations between positions, movements, and/or portions of a patient's body and health conditions, which may be defined in the electronic health record data. In some embodiments, knowledge corpus module 165 may analyze positions and/or movements of a patient in combination with other data, such as time-series audio data, to map particular positions and movements to health conditions when those positions and/or movements are associated with utterances of the patient that are indicative of pain. Knowledge corpus 165 may update the knowledge corpus over time with new data acquired from a patient, and may detect when changes to the knowledge corpus indicate a change in a health condition of a patient.

Thus, knowledge corpus module 165 may build a knowledge corpus for a patient in which particular positions, movements, and/or portions of a patient's body are mapped to health conditions. Knowledge corpus module 165 may, based on a lack of any associations of positions, movements, and/or portions of a patient's body to a health condition, identify those positions, movements, and/or portions of the patient's body as unaffected by a health condition. In some embodiments, knowledge corpus module 165 employs a rules-based approach to mapping particular positions, movements, and/or portions of a patient's body to a health condition. In a rules-based approach, rules may be defined that classify each position and movement of a patient's body as related or unrelated to a health condition. Rules may be provided to classify particular positions as being unrelated to a health condition if a patient occupies those positions a predetermined amount of time, such as a threshold percentage of the day. Additionally or alternatively, rules may be provided to classify certain movements of a patient's body as related or unrelated to a health condition based on a number of movements performed over a span of time. For example, if a patient uses a left arm frequently and a right arm infrequently, a rule may indicate that motion in patient's right arm is associated with pain or injury. Rules may be provided to further determine a magnitude of association between a position, movement, and/or portion of a patient's body and the health condition. In particular, a rule may indicate that longer avoidance of a particular position or movement is associated with an increasingly-higher association with a health condition.

In some embodiments, knowledge corpus module 165 employs conventional or other machine learning techniques to map particular positions, movements, and/or portions of a patient's body to a health condition. A machine learning model may include a conventional or other model type, such as a neural network, a support vector machine, a Hidden Markov model, an adversarial network model, and the like. A machine learning model may be trained to classify positions, movements, and/or portions of a patient's body as either affected or unaffected by a health condition based on input data that includes the identified positions and movements of the patient over time. In particular, a supervised machine learning model can be trained using training data that includes positions and/or movements of patients that are each provided with a label indicating whether that position or movement is associated with a health condition, and if so, a magnitude of the health condition. Thus, the machine learning model may be trained to output mappings of health conditions to positions, movements, and/or portions of a patient's body. Additionally or alternatively, a machine learning model may be trained using training data that contains examples of past mappings of knowledge corpus module 165 that were used to provide care to previous patients and are tagged with positive or negative patient outcomes (e.g., indications of whether the patient's recovery was satisfactory). Thus, knowledge corpus module 165 may learn from successful previous mappings to more accurately map health conditions to positions, movements, and/or portions of a patient's body.

Patient monitoring module 170 may monitor a patient associated with electronic textile device 105 by comparing current positions and/or movements of a patient to the knowledge corpus. Patient monitoring module 170 may receive updated data indicating current positions and/or movements of a patient that is generated by biometric data processing module 160 as a result of processing the biometric data obtained from electronic textile device 105. Patient monitoring module 170 may compare the identified positions and/or movements of the patient to policies or rules that indicate unsafe positions and/or movements to determine whether a current position or movement is associated with a health condition of the patient. Thus, patient monitoring module 170 can determine if a patient's current position or movement is associated with pain or injury. In response to determining that a patient's current position or movement may be painful or harmful to a patient, patient monitoring module 170 can transmit an alert to one or more users, such as a user of client device 110 or other health care provider. In some embodiments, patient monitoring module 170 may transmit instructions to electronic textile device 105 based on an identified position and/or movement of the patient violating a policy indicated by the knowledge corpus. The transmitted instructions may cause electronic textile device 105 to perform one or more actions. In some embodiments, electronic textile device 105 includes heating elements, which may be activated to soothe an area of the patient indicated by the instructions of patient monitoring module 170. In some embodiments, electronic textile device 105 includes lighting elements, such as light emitting diodes (LEDs), which are activated to draw attention to a particular portion of the patient's body indicated by the instructions of electronic textile device 105.

Treatment plan module 175 generates treatment plans that are personalized to a patient and are based on the patient's knowledge corpus. Treatment plan module 175 may utilize a rules-based approach in which mappings in the knowledge corpus are converted to health care instructions. In particular, treatment plan module 175 may generate treatment plans that outline the positions, movements, and/or portions of a patient's body that are associated with a health condition and the positions, movements, and/or portions of a patient's body that are not associated with a health condition. In particular, a treatment plan may indicate one or more positions, movements, and/or portions of a patient's body that a health care provider should avoid and/or help the patient avoid.

Additionally or alternatively, treatment plans may include visualizations to describe positions, movements, and/or portions of a patient's body that should be avoided. Based on the mappings in a patient's knowledge corpus, treatment plan module 175 may select stock images from a database, such as database 180, displaying the positions, movements, and/or portions of a patient's body to avoid. In some embodiments, treatment plan module 175 may generate visualizations based on a patient's knowledge corpus and/or data obtained from electronic textile device 105 to present augmented reality views that correspond to locations on a patient's body that should be avoided. In some embodiments, the augmented reality views may represent quantitative data from the knowledge corpus such as pain ratings for various portions of the body, which can be determined based on the degree of relatedness of a portion of a patient's body to a health condition. Thus, a treatment plan may include a visualization such as a heat map or numerical labels presented over various portions of a patient's body to indicate pain levels.

Database 180 may include any non-volatile storage media known in the art. For example, database 180 can be implemented with a tape library, optical library, one or more independent hard disk drives, or multiple hard disk drives in a redundant array of independent disks (RAID). Similarly, data in database 180 may conform to any suitable storage architecture known in the art, such as a file, a relational database, an object-oriented database, and/or one or more tables. In some embodiments, database 180 may store data including time-series biometric data and identified position and/or movement data, knowledge corpus data, and treatment plan data.

Network 185 may include a local area network (LAN), a wide area network (WAN) such as the Internet, or a combination of the two, and includes wired, wireless, or fiber optic connections. In general, network 185 can be any combination of connections and protocols known in the art that will support communications between electronic textile device 105, client device 110, augmented reality device 130, and/or health care server 150 via their respective network interfaces in accordance with embodiments of the present invention.

Figure 2:
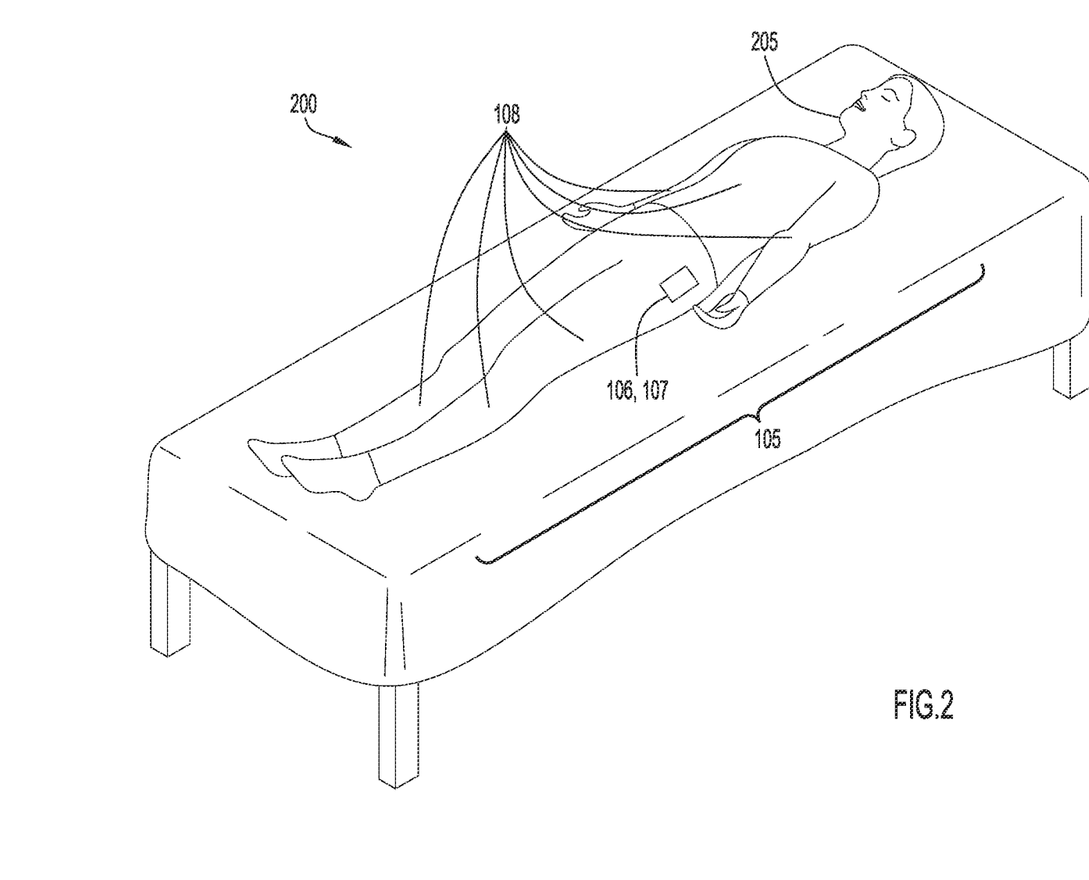
FIG. 2 is a diagram depicting a user environment in accordance with an embodiment of the present invention.

FIG. 2 is a diagram depicting a user environment 200 in accordance with an embodiment of the present invention. As depicted, a patient 205 is outfitted with an electronic textile device 105 that is implemented as clothing similar to long-sleeved shirt and long pants. Patient 205 may be a patient receiving health care, either in a health care facility, at home, or otherwise. Electronic textile device 105 may include a portion in which a network interface (I/F) 106 and at least one processor 107 are positioned. A plurality of sensors 108 may be distributed throughout the woven material of electronic textile device 105 in order to collect data about patient 205 that can be used to determine a position of patient 205 as well as identify or detect movement of patient 205.

Figure 3A:
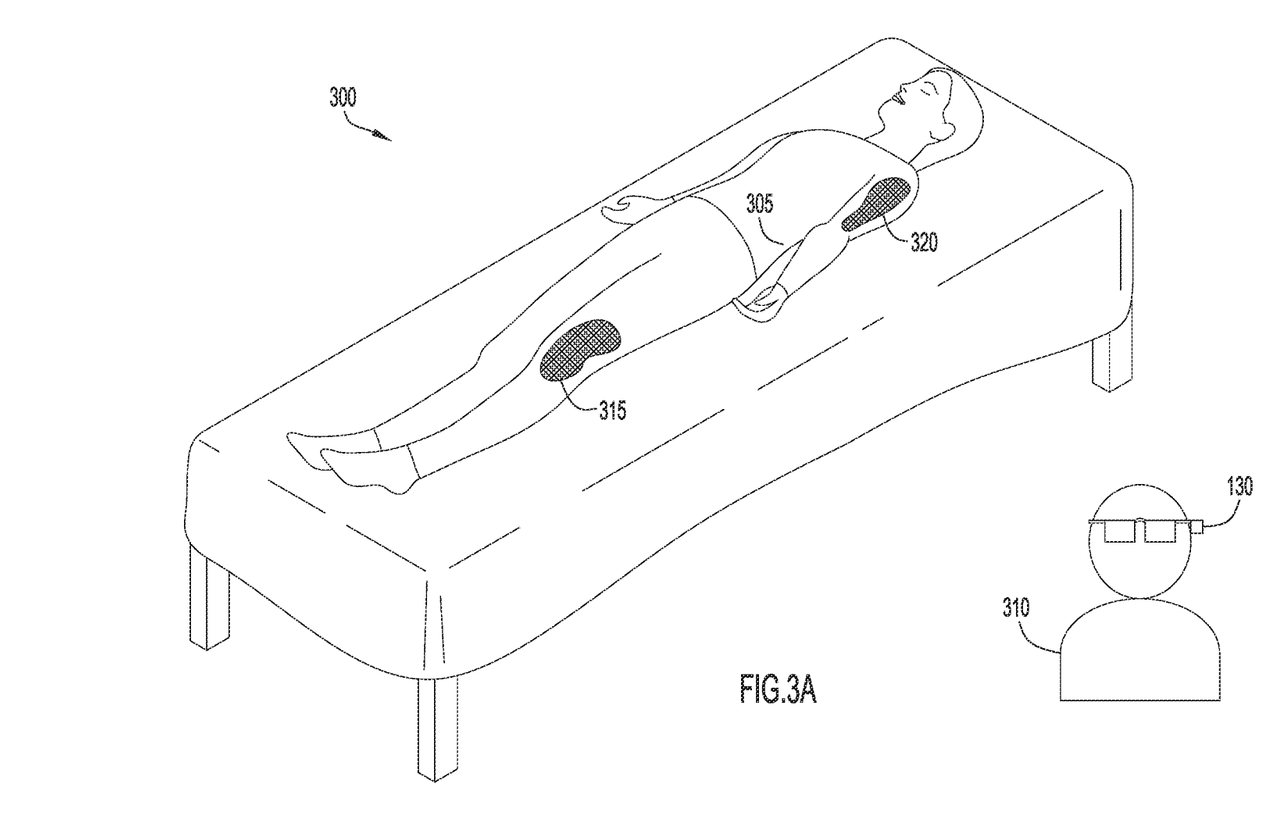
FIG. 3A is a diagram depicting a user environment with augmented reality visualizations in accordance with an embodiment of the present invention.

FIG. 3A is a diagram depicting a user environment 300 with augmented reality visualizations in accordance with an embodiment of the present invention. As depicted, user environment 300 includes a patient 305 and a health care provider 310 equipped with augmented reality device 130. Visualizations 315 and 320 may include augmented reality elements that are presented to health care provider 310 via augmented reality device 130 in a manner that overlays visualizations 315 and 320 on a particular position of the body of patient 305, as seen from the perspective of health care provider 310. Thus, visualization 315 and 320 may indicate portions of the body of patient 305 that should be avoided, thereby providing health care provider 310 with a visual reminder that improves the quality of health care provided.

Figure 3B:
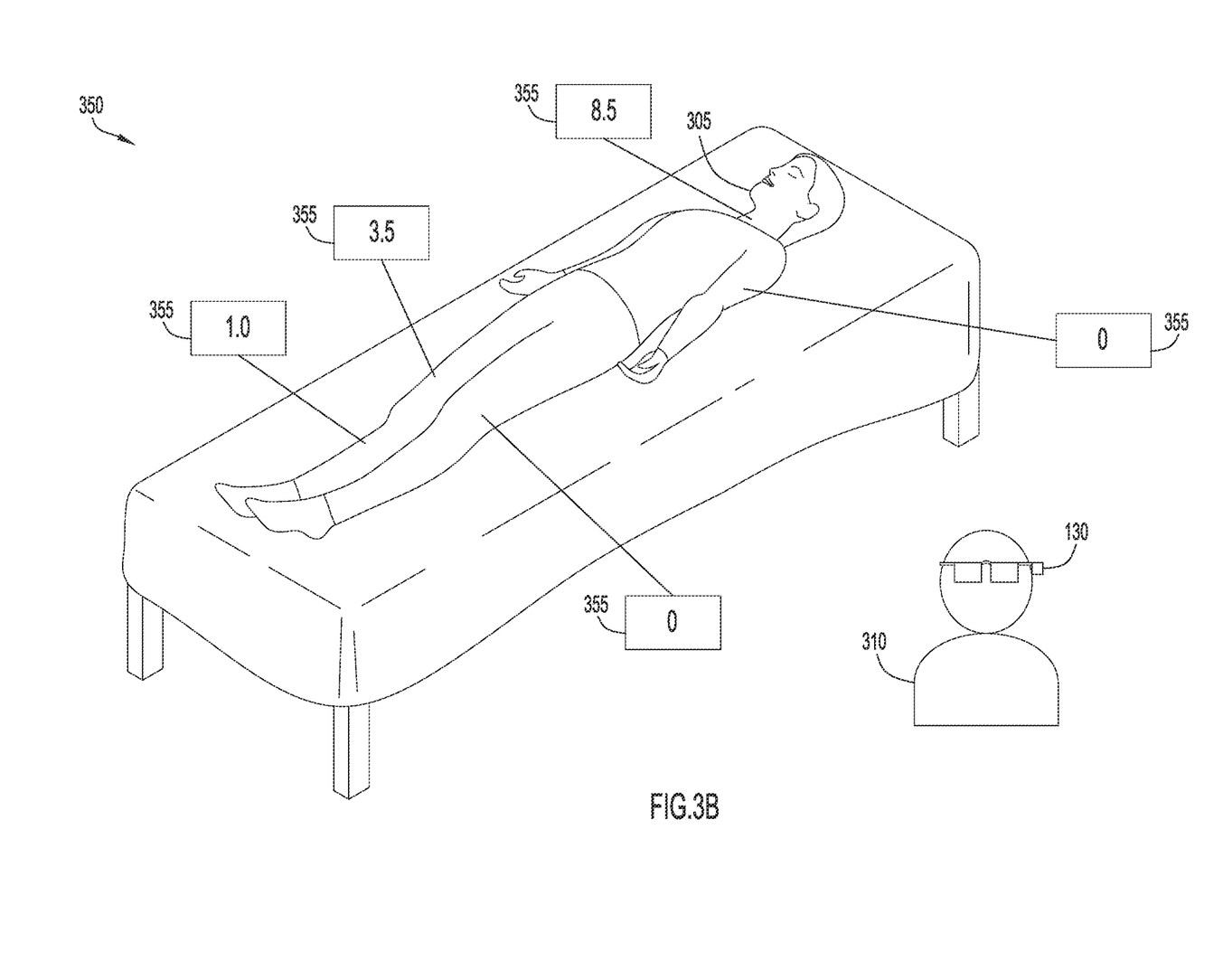
FIG. 3B is a diagram depicting a user environment with augmented reality visualizations in accordance with an embodiment of the present invention.

FIG. 3B is a diagram depicting a user environment 350 with augmented reality visualizations in accordance with an embodiment of the present invention. As depicted, user environment 350 includes a patient 305 and a health care provider 310 equipped with augmented reality device 130. Visualizations 355 may include augmented reality elements that are presented to health care provider 310 via augmented reality device 130 in a manner that overlays visualizations 355 adjacent to a particular position of the body of patient 305, as seen from the perspective of health care provider 310. For example, visualizations 355 may include floating or hovering boxes containing numbers with lines indicating particular portions of the body of patient 305 to which each visualization 355 applies. In the depicted embodiment, visualizations 355 may include pain ratings for various portions of the body of patient 305.

Figure 4:
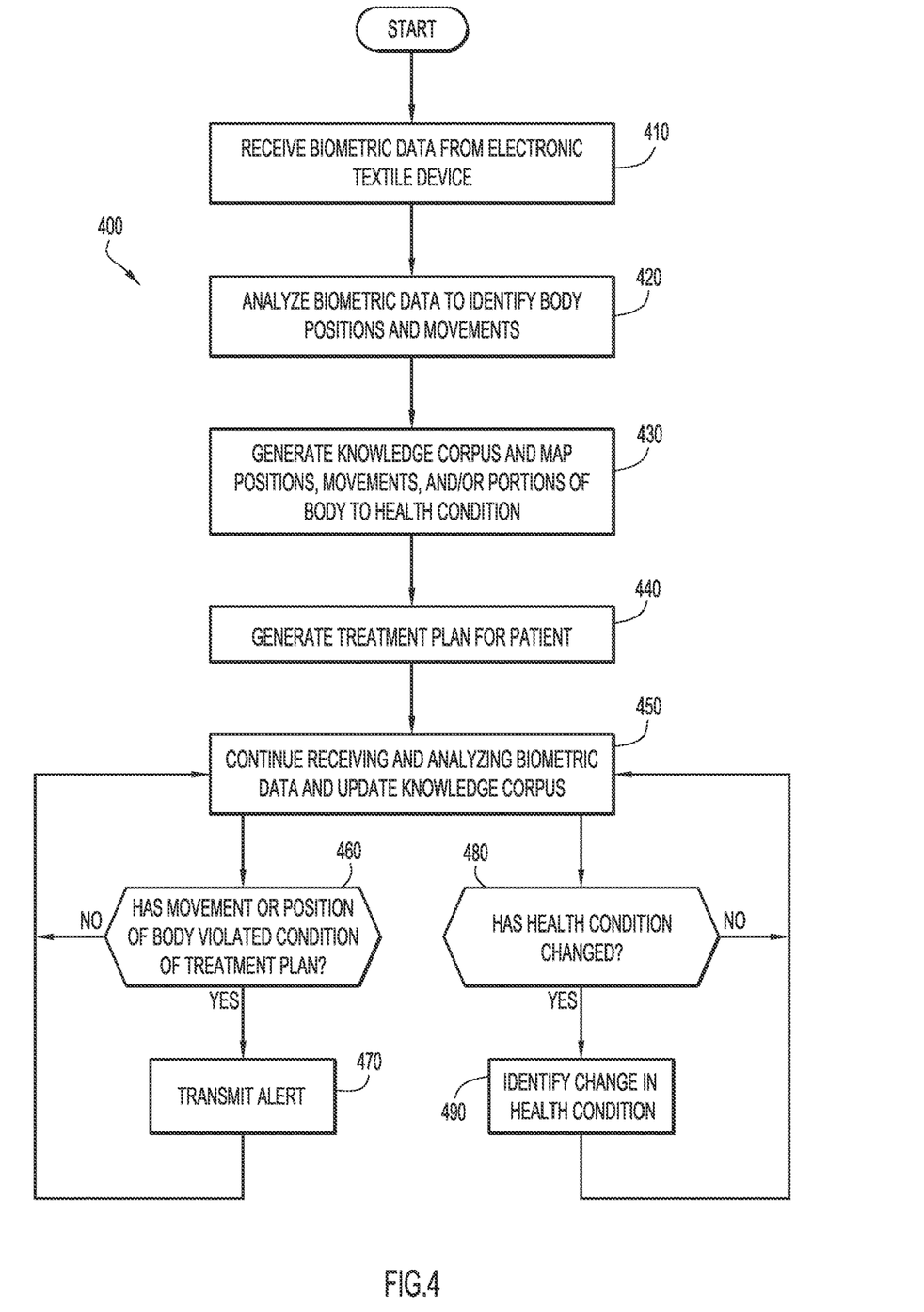
FIG. 4 is a flow chart depicting a method of monitoring and treating a patient in accordance with an embodiment of the present invention

FIG. 4 is a flow chart depicting a method 400 of monitoring and treating a patient in accordance with an embodiment of the present invention.

Biometric data is received from an electronic textile device at operation 410. Biometric data may be collected from an electronic textile device that is associated with a patient, such as electronic textile device 105. The biometric data may include data collected from a plurality of sensors in the electronic textile device, such as pressure data, temperature data, stress data, strain data, acceleration data, and the like. Biometric data may be received by a server, such as health care server 150, for further analysis.

The biometric data is analyzed to identify positions and/or movements at operation 420. As biometric data is gathered via sensors with known positions with respect to a patient's body, the biometric data can be analyzed to determine a body position occupied by the patient at a particular time, or to identify a movement of the patient at a particular time. Positions and/or movements may be identified with respect to time to measure how long each position is occupied by the patient, how frequently the patient engages in a particular movement, and the like.

A knowledge corpus is generated and populated with mappings of positions, movements, and/or portions of the body of the patient to health conditions of the patient at operation 430. The identified body positions and movements of a patient over time can be analyzed in order to identify which positions and movements, and therefore, portions of a body, are associated with pain or injury of the patient. In particular, positions and movements can be analyzed over time to identify favored and disfavored positions and movements, and disfavored positions and movements can be associated with a health condition (e.g., pain or injury). The knowledge corpus may be updated continuously as new data becomes available.

A treatment plan is generated for the patient at operation 440. The treatment plan may include personalized guidelines for providing health care to a patient that are based on the patient's knowledge corpus. Treatment plans can be generated using a rules-based approach and/or a machine learning approach in which mappings in the knowledge corpus are converted to health care instructions. In particular, a treatment plan is generated by converting the positions, movements, and/or portions of a patient's body that are associated with a health condition into instructions for health care providers, such as instructions to avoid interacting with particular portions of the patient's body or to use extreme care when interacting with those portions. Thus, a treatment plan may indicate one or more positions, movements, and/or portions of a patient's body that a health care provider should avoid and/or help the patient avoid.

Biometric data continues to be received and analyzed and the knowledge corpus is updated accordingly at operation 450. Operation 460 determines whether a movement or position of the patient's body has violated a condition of the treatment plan. If there is no movement or body position that is determined to violate a condition of the treatment plan, biometric data continues to be received and analyzed and the knowledge corpus is updated at operation 450. If the patient performs a movement or begins to occupy a body position that is associated with a health condition, then an alert is transmitted at operation 470. The alert may be transmitted to one or more computing devices associated with health care providers so they can render care to the patient in the event that the movement or position is causing the patient pain or injury. After transmitting an alert at operation 470, biometric data continues to be received and analyzed and the knowledge corpus is updated at operation 450.

Operation 480 determines whether a health condition of the patient has changed. If there is no change in health condition indicated by analysis of subsequently-received biometric data, then the biometric data continues to be received and analyzed and the knowledge corpus is updated at operation 450. If analyzing the biometric data indicates that there is a new mapping of a position, movement, and/or portion of the body of the patient to a health condition, or a former mapping is subsequently no longer indicated by the biometric data for a threshold period of time, then the change is identified at operation 490. The change may be identified based on a notification and/or may be included in an updated treatment plan. After indicating the changed health condition at operation 490, biometric data continues to be received and analyzed and the knowledge corpus is updated at operation 450.

Figure 5:
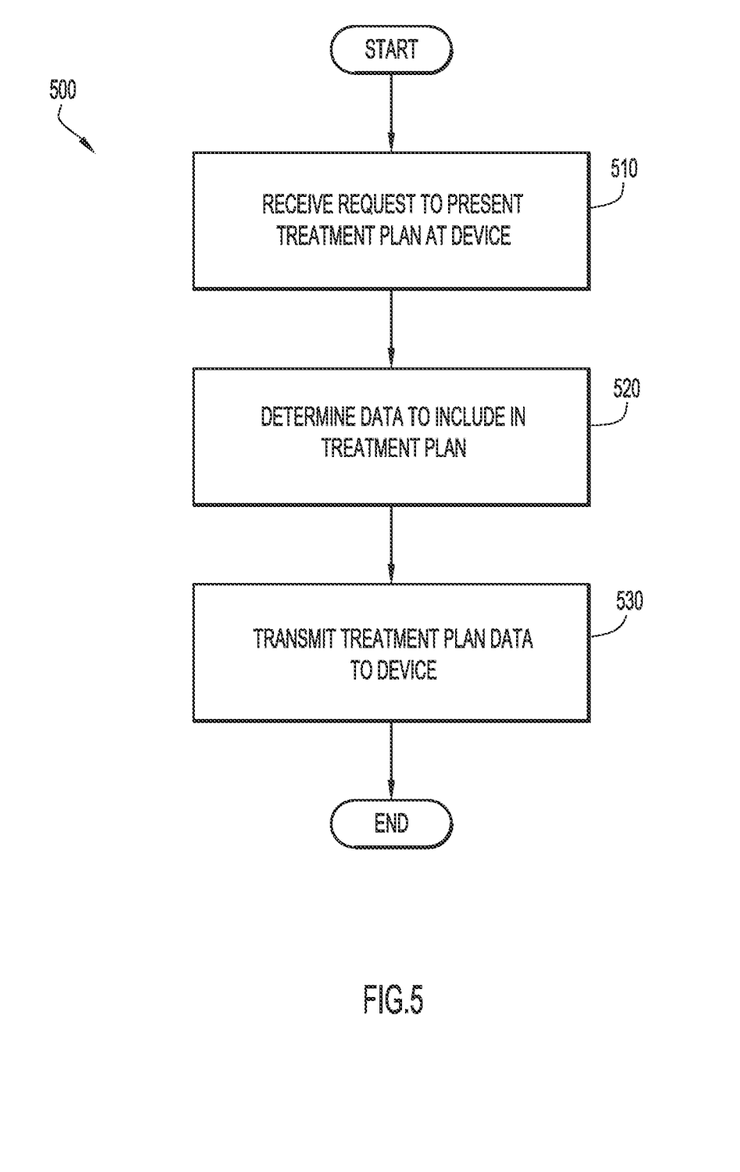
FIG. 5 is a flow chart depicting a method of presenting a treatment plan in accordance with an embodiment of the present invention.

FIG. 5 is a flow chart depicting a method 500 of presenting a treatment plan in accordance with an embodiment of the present invention.

A request to present a treatment plan at a device is received at operation 510. A device, such as client device 110 and/or augmented reality device 130, may transmit a request to a server, such as health care server 150, to obtain a treatment plan for a patient. In some embodiments, a health care provider authenticates at client device 110 and/or augmented reality device 130 to ensure that an authorized user is able to obtain the treatment plan and/or other patient data. Thus, by requiring authorization, present invention embodiments can comply with any statutory requirements relating to the protection of patient data. In some embodiments, a smart contract-type authentication system may be implemented using a cryptographic blockchain or by other conventional or non-conventional techniques.

The data to be included in the treatment plan is determined at operation 520. Initially, health care server 150 identifies treatment plan data associated with the patient indicated in the received request. Next, treatment plan module 175 may select or generate one or more visualizations based on the requesting entity. In particular, when the requesting device indicates that it is capable of augmented reality display, then data corresponding to an augmented reality visualization is included in the treatment plan. Otherwise, the treatment plan may include visualizations such as images or videos corresponding to positions, movements, and/or portions of a patient's body that should be avoided or treated with care. Additionally or alternatively, treatment plan data may include a text description of the treatment plan.

The treatment plan data is transmitted to the device at operation 530. Once the treatment plan data is received, a user, such as a health care provider, can review the treatment plan, view visualizations, and the like.

Figure 6:
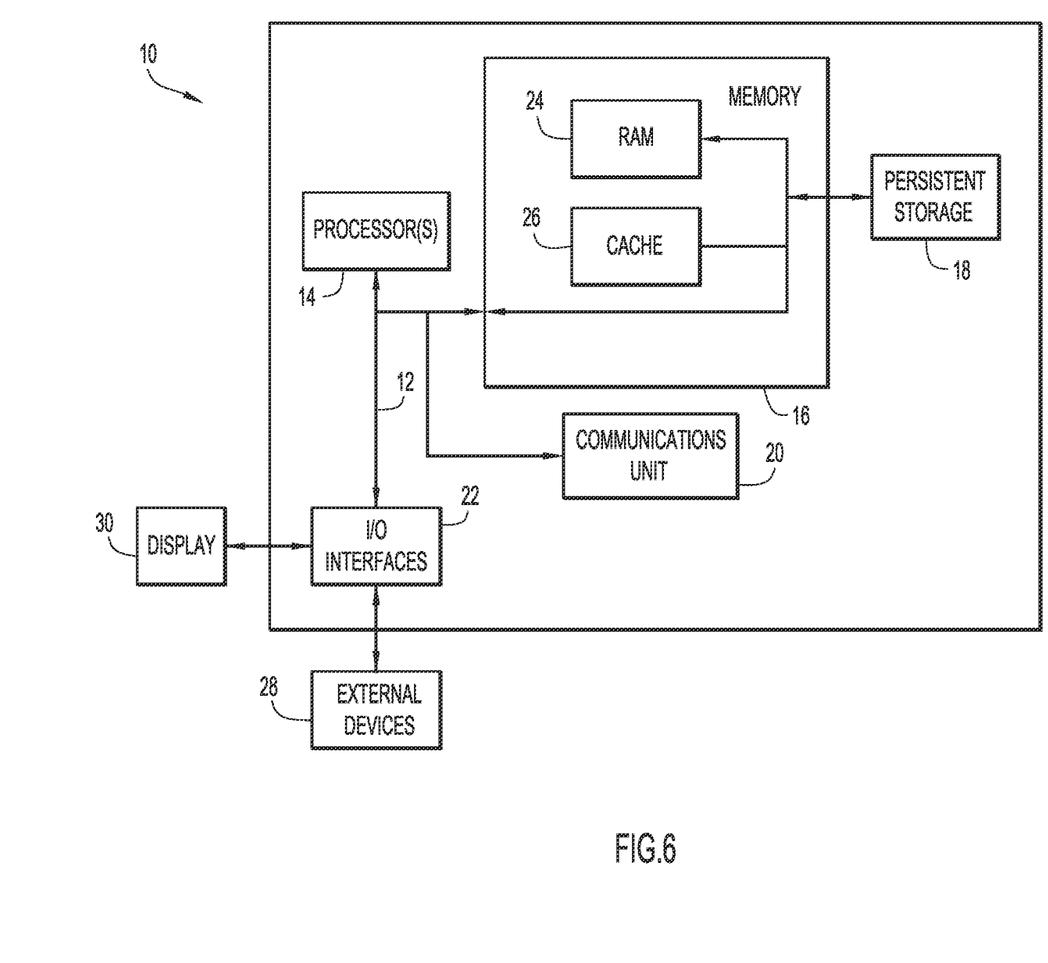
FIG. 6 is a block diagram depicting a computing device in accordance with an embodiment of the present invention.

FIG. 6 is a block diagram depicting components of a computer 10 suitable for executing the methods disclosed herein. Computer 10 may implement client device 110, augmented reality device 130, and/or health care server 150 in accordance with embodiments of the present invention. It should be appreciated that FIG. 6 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to patient monitoring and treatment using electronic textiles (e.g., biometric data, knowledge base data, treatment plan data, visualization data, etc.) may be stored within any conventional or other data structures (e.g., files, arrays, lists, stacks, queues, records, etc.) and may be stored in any desired storage unit (e.g., database, data or other repositories, queue, etc.). The data transmitted between electronic textile device 105, client device 110, augmented reality device 130 and/or health care server 150 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to patient monitoring and treatment using electronic textiles (e.g., biometric data, knowledge base data, treatment plan data, visualization data, etc.) may include any information provided to, or generated by, electronic textile device 105, client device 110, augmented reality device 130 and/or health care server 150. Data relating to patient monitoring and treatment using electronic textiles may include any desired format and arrangement, and may include any quantity of any types of fields of any size to store any desired data. The data relating to patient monitoring and treatment using electronic textiles may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to patient monitoring and treatment using electronic textiles), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of improving patient monitoring and treatment using electronic textiles.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., communications software, server software, client module 125, augmented reality display module 154, biometric data processing module 160, knowledge corpus module 165, patient monitoring module 170, treatment plan module 175, etc.). These systems may include any types of monitors and input devices (e.g., keyboard, mouse, voice recognition, etc.) to enter and/or view information.

It is to be understood that the software (e.g., communications software, server software, client module 125, augmented reality display module 154, biometric data processing module 160, knowledge corpus module 165, patient monitoring module 170, treatment plan module 175, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., communications software, server software, client module 125, augmented reality display module 154, biometric data processing module 160, knowledge corpus module 165, patient monitoring module 170, treatment plan module 175, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to patient monitoring and treatment using electronic textiles). The database system may be implemented by any number of any conventional or other databases, data stores or storage structures (e.g., files, databases, data structures, data or other repositories, etc.) to store information (e.g., data relating to patient monitoring and treatment using electronic textiles). The database system may be included within or coupled to the server and/or client systems. The database systems and/or storage structures may be remote from or local to the computer or other processing systems, and may store any desired data (e.g., data relating to patient monitoring and treatment using electronic textiles).

The present invention embodiments may employ any number of any type of user interface (e.g., Graphical User Interface (GUI), command-line, prompt, etc.) for obtaining or providing information (e.g., data relating to patient monitoring and treatment using electronic textiles), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, providing improved health care to patients by identifying and treating health conditions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for patient monitoring and treatment using electronic textiles, the method comprising:
receiving biometric data pertaining to a user, wherein the biometric data is obtained over time from an electronic textile device associated with a body of the user, wherein the electronic textile device includes a plurality of elements corresponding to one or more particular locations of the body of the user, the plurality of elements including pressure sensing elements, and one or more heating elements;
analyzing the biometric data to identify positions and movements of the body of the user;
analyzing the identified positions and movements of the body to generate a knowledge corpus for the user that maps one or more of: positions, movements, and portions of the body to a health condition of the user, wherein the identified positions include a side of the body of the user that is in contact with a bed, and wherein the analysis classifies a particular identified position of the body of the user as being unrelated to the health condition of the user if the user occupies the particular identified position for at least a predetermined amount of time;
generating a treatment plan for the user based on the knowledge corpus, wherein the treatment plan indicates a relatedness between the health condition of the user and the one or more positions, movements, and portions of the body;
presenting, to a health care practitioner, a visualization of the relatedness between the health condition of the user and the one or more positions, movements, and portions of the body, wherein the visualization comprises augmented reality data that is presented to a health care provider via an augmented reality display device, and wherein the visualization presents a heat map of portions of the body that are associated with positions and movements that are specific to a particular disease of the patient while omitting from the heatmap other movements or positions of the body that are not specific to the particular disease; and
activating the one or more heating elements at an area of the body of the patient that corresponds to the side of the body of the patient that is determined based on the treatment plan by analyzing the identified positions and movements of the body, wherein the one or more heating elements of the electronic textile device are activated by transmitting instructions to the electronic textile device.

2. The computer-implemented method of claim 1, wherein the health condition includes one or more of: a sensation of pain, and an injury corresponding to a mobility of the patient.

3. The computer-implemented method of claim 2, further comprising:
in response to determining that the body of the user occupies a position, or has performed a movement, that is associated with the sensation of pain or the injury, transmitting an alert to notify a health care provider.

4. The computer-implemented method of claim 1, wherein the treatment plan includes a recommendation of one or more particular positions in which to place the body to treat the health condition of the user.

5. The computer-implemented method of claim 1, wherein the knowledge corpus is updated over time, and further comprising:
analyzing changes in the knowledge corpus to identify an improvement or a worsening of the health condition of the user.

6. The computer-implemented method of claim 1, further comprising:
identifying, using the knowledge corpus, one or more portions of the body associated with pain or injury; and
wherein the heat map indicates relative sensitivity to pain or injury for each of the one or more portions of the body.

7. A computer system for patient monitoring and treatment using electronic textiles, the computer system comprising:
one or more computer processors;
one or more computer readable storage media;
program instructions stored on the one or more computer readable storage media for execution by at least one of the one or more computer processors, the program instructions comprising instructions to:
receive biometric data pertaining to a user, wherein the biometric data is obtained over time from an electronic textile device associated with a body of the user, wherein the electronic textile device includes a plurality of elements corresponding to one or more particular locations of the body of the user, the plurality of elements including pressure sensing elements, and one or more heating elements;
analyze the biometric data to identify positions and movements of the body of the user;
analyze the identified positions and movements of the body to generate a knowledge corpus for the user that maps one or more of: positions, movements, and portions of the body to a health condition of the user, wherein the identified positions include a side of the body of the user that is in contact with a bed, and wherein the analysis classifies a particular identified position of the body of the user as being unrelated to the health condition of the user if the user occupies the particular identified position for at least a predetermined amount of time;
generate a treatment plan for the user based on the knowledge corpus, wherein the treatment plan indicates a relatedness between the health condition of the user and the one or more positions, movements, and portions of the body;
present, to a health care practitioner, a visualization of the relatedness between the health condition of the user and the one or more positions, movements, and portions of the body, wherein the visualization comprises augmented reality data that is presented to a health care provider via an augmented reality display device, and wherein the visualization presents a heat map of portions of the body that are associated with positions and movements that are specific to a particular disease of the patient while omitting from the heatmap other movements or positions of the body that are not specific to the particular disease; and
activate the one or more heating elements of the electronic textile device at an area of the body of the patient that corresponds to the side of the body of the patient that is determined based on the treatment plan by analyzing the identified positions and movements of the body, wherein the one or more heating elements of the electronic textile device are activated by transmitting instructions to the electronic textile device.

8. The computer system of claim 7, wherein the health condition includes one or more of: a sensation of pain, and an injury corresponding to a mobility of the patient.

9. The computer system of claim 8, wherein the program instructions further comprise instructions to:
in response to determining that the body of the user occupies a position, or has performed a movement, that is associated with the sensation of pain or the injury, transmit an alert to notify a health care provider.

10. The computer system of claim 7, wherein the treatment plan includes a recommendation of one or more particular positions in which to place the body to treat the health condition of the user.

11. The computer system of claim 7, wherein the knowledge corpus is updated over time, and wherein the program instructions further comprise instructions to:
analyze changes in the knowledge corpus to identify an improvement or a worsening of the health condition of the user.

12. The computer system claim 7, wherein the program instructions further comprise instructions to:
identify, using the knowledge corpus, one or more portions of the body associated with pain or injury; and
wherein the heat map indicates relative sensitivity to pain or injury for each of the one or more portions of the body.

13. A computer program product for patient monitoring and treatment using electronic textiles, the computer program product comprising one or more computer readable storage media collectively having program instructions embodied therewith, the program instructions executable by a computer to cause the computer to:
receive biometric data pertaining to a user, wherein the biometric data is obtained over time from an electronic textile device associated with a body of the user, wherein the electronic textile device includes a plurality of elements corresponding to one or more particular locations of the body of the user, the plurality of elements including pressure sensing elements, and one or more heating elements;
analyze the biometric data to identify positions and movements of the body of the user;
analyze the identified positions and movements of the body to generate a knowledge corpus for the user that maps one or more of: positions, movements, and portions of the body to a health condition of the user, wherein the identified positions include a side of the body of the user that is in contact with a bed, and wherein the analysis classifies a particular identified position of the body of the user as being unrelated to the health condition of the user if the user occupies the particular identified position for at least a predetermined amount of time;
generate a treatment plan for the user based on the knowledge corpus, wherein the treatment plan indicates a relatedness between the health condition of the user and the one or more positions, movements, and portions of the body;
present, to a health care practitioner, a visualization of the relatedness between the health condition of the user and the one or more positions, movements, and portions of the body, wherein the visualization comprises augmented reality data that is presented to a health care provider via an augmented reality display device, and wherein the visualization presents a heat map of portions of the body that are associated with positions and movements that are specific to a particular disease of the patient while omitting from the heatmap other movements or positions of the body that are not specific to the particular disease; and
activate the one or more heating elements at an area of the body of the patient that corresponds to the side of the body of the patient that is determined based on the treatment plan by analyzing the identified positions and movements of the body, wherein the one or more heating elements of the electronic textile device are activated by transmitting instructions to the electronic textile device.

14. The computer program product of claim 13, wherein the health condition includes one or more of: a sensation of pain, and an injury corresponding to a mobility of the patient.

15. The computer program product of claim 14, wherein the program instructions further cause the computer to:
in response to determining that the body of the user occupies a position, or has performed a movement, that is associated with the sensation of pain or the injury, transmit an alert to notify a health care provider.

16. The computer program product of claim 13, wherein the treatment plan includes a recommendation of one or more particular positions in which to place the body to treat the health condition of the user.

17. The computer program product of claim 13, wherein the knowledge corpus is updated over time, and wherein the program instructions further cause the computer to:
analyze changes in the knowledge corpus to identify an improvement or a worsening of the health condition of the user.

* * * * *